United States Patent [19]

Schachar et al.

[11] Patent Number: 4,520,816

[45] Date of Patent: Jun. 4, 1985

[54] METHOD AND APPARATUS FOR DELIVERING LASER ENERGY FOR OPHTHALMIC USE

[76] Inventors: Ronald A. Schachar, 1020 N. Highway 75, Denison, Tex. 75020; Stuart A. Solin, 1740 Shaker Blvd., Okemos, Mich. 48864

[21] Appl. No.: 457,433

[22] Filed: Jan. 12, 1983

[51] Int. Cl.³ .................... A61B 3/00; A61B 17/36
[52] U.S. Cl. .................... 128/303.1; 128/395; 128/397; 219/121 LB; 219/121 LS; 219/121 LT; 351/200
[58] Field of Search ............ 219/121 LA, 121 LB, 219/121 LS, 121 LU, 121 L, 121 LM; 128/303.1, 395, 396–398; 351/200–201; 372/14–15; 356/365; 331/DIG. 1, 61, 78

[56] References Cited

U.S. PATENT DOCUMENTS

| | | | |
|---|---|---|---|
| 2,235,319 | 3/1941 | Jobe | 351/200 |
| 3,369,101 | 2/1968 | Curcio | 219/121 LU |
| 3,703,176 | 11/1972 | Vassiliadis et al. | 128/303.1 |
| 3,710,798 | 1/1973 | Bredemeier | 219/121 LS |
| 3,750,670 | 8/1973 | Palanos et al. | 128/395 |
| 3,828,788 | 8/1974 | Krasnov et al. | 128/303.1 |
| 4,408,602 | 10/1983 | Nakajima | 219/121 LS |

OTHER PUBLICATIONS

IBM Technical Disclosure Bulletin, vol. 6, No. 12, May 1964, pp. 57–58.
Cavitron Model 3000 Argon Photocoagulation Laser, Cavitron Surgical Systems, 1980.

*Primary Examiner*—C. Fred Rosenbaum
*Assistant Examiner*—Gene B. Kartchner
*Attorney, Agent, or Firm*—Jerry W. Mills; Gregory M. Howison; Nina L. Medlock

[57] ABSTRACT

An ophthalmic laser surgery system includes a slit lamp (14) with an illuminator (16) and a biomicroscope (26). The high power laser (34) delivers a laser beam (36) which is mixed with the output from a lower power laser (38) with a dichroic mirror (54). The output of the dichroic mirror (54) is input to the harmonic generator (60) to generate harmonics thereof. The output of the harmonic generator (60) is optically directed to move along the rotational axis through rotational supports (22) and (30). The laser beam is then directed by mirrors (72) and (80) to a focusing lens (90) and a filter (92) to a dielectric mirror (94). The dielectric mirror (94) mixes the illumination from the slit lamp (14) with the laser beam for delivery to the eye (12). A micromanipulator (102) adjusts the position of the dielectric mirror (94). A control circuit (104) controls the operation of the laser (34). A protection device (110) has filters for disposal within the path of the viewing axis of the biomicroscope to prevent damage to the surgeon's eyes.

2 Claims, 8 Drawing Figures

METHOD AND APPARATUS FOR DELIVERING LASER ENERGY FOR OPHTHALMIC USE

TECHNICAL FIELD

The present invention pertains in general to surgical eye lasers and, more particularly, to the combination of a laser and a slit lamp for use in eye surgery.

BACKGROUND OF THE INVENTION

Lasers have been utilized for some time in eye surgery for delivering short bursts of high energy coherent light. They have proved useful in various eye operations such as capsulotomies and vitreous removals. Unlike other surgical techniques utilizing lasers, eye surgery requires that the laser be focused on a portion of the eye that is interior to the cornea. In so doing, it is necessary to expand the laser beam prior to entering the surface of the cornea and then focus it on the other side of the cornea interior to the eye itself. In this manner, the destructive energy of the laser is only focused at a certain point on the interior surface of the eye or on a point within an area of the eye such as the lens.

In addition to delivering the laser energy internal to the eye, it is also necessary for a surgeon to very carefully locate the point at which the laser beam focuses since even a slight deviation in positioning of the laser beam prior to cutting can be disastrous. For example, if the laser beam were to accidentally be focused on the macula of the eye, a patient could be permanently blinded. It is therefore necessary for a surgeon to have adequate control over the power level of the laser in addition to having the capability of finely positioning the focal point of the laser such that this positioning is both reliable and accurate in addition to possessing a high degree of stability.

Since positioning is of paramount importance, it is necessary to utilize a system that delivers the laser energy within the viewing area of the surgeon. The surgeon can utilize either an opthalmoscope or, more commonly, a slit lamp which is comprised of a biomicroscope for viewing the eye and a slit lamp for rotation about the periphery of the eye for illumination thereof. In present systems, the laser is delivered through optics along the viewing axis of the biomicroscope such that the surgeon can locate the area to be operated upon and then activate the laser to perform the actual surgery. Since the viewing axis is normally perpendicular to the eye, this can have disastrous effects in that the sensitive portions of the eyes, such as the macula, are in close proximity thereto. For example, when operating upon cataracts, it is possible for the laser to accidently impinge upon the macula. These types of systems have no capability for delivering the laser along any path other than the viewing axis.

The type of laser utilized for surgery depends upon the particular operation. For operations that coagulate tissue, a laser emitting in the green region is normally utilized since red tissue absorbs heavily in the green region. In other applications, however, an infrared laser is utilized to deliver large amounts of power. It has been necessary in prior art systems to have separate lasers available to generate the particular frequencies that are found most useful in the surgical process.

In view of the above disadvantages with the prior art in positioning a laser for surgical use, it is desirable to provide a laser delivery system for ophthalmic use that provides laser energy that is not perpendicular to the eye and also has the versatility of outputting a multiplicity of frequencies or wavelengths.

SUMMARY OF THE INVENTION

The present invention disclosed and claimed herein comprises a method and apparatus for delivering laser energy to the eye for ophthalmic purposes. The apparatus includes a biomicroscope mounted for movement about a rotational axis to traverse a first arc and a slit lamp for illumination of the eye mounted for movement about the rotational axis to traverse a second arc that has a shorter length than the first arc. A main laser beam is generated by a laser and the beam is optically directed along the illumination path of the slit lamp such that the laser beam is movable with the slit lamp and capable of being adjusted off axis with respect to the viewing axis of the biomicroscope. A focusing device disposed in the laser beam allows the laser beam to be focused in the area of the eye illuminated by the slit lamp.

In another embodiment of the present invention, the laser outputs a high power laser beam for use in surgical operations that is controlled by a control circuit that controls the duration and power level thereof. A second laser is utilized to generate two parallel low power laser beams that are transmitted and directed along with the high power laser beam and focused therewith. The two low power laser beams emit in the visible region and allow an operator to focus the laser directing optics thereby focusing the low power laser beams. This permits the system to be focused prior to turning on the high power laser beam which is parfocal with the low power laser beams thus preventing lasing of an unintended area of the eye.

In yet another embodiment of the present invention, a beam expander is disposed in the path of the laser beam to disperse the power contained therein over a broader area, thereby reducing the power per square unit of area. The high power laser beam is processed through a harmonic generator to generate harmonics thereof in different areas of the spectrum. A filter disposed in the expanded portion of the beam or any part of the beam after the harmonic generator is utilized to select the appropriate harmonic for the appropriate operation to be performed on the eye. This filter is selectable such that any of the harmonics generated can be individually selected. Further, to protect the eyes of the surgeon when viewing the eye through the biomicroscope, a shutter and/or an absorbing filter is disposed along the viewing axis to reject or absorb any reflected energy for the high power laser that may travel along the viewing axis. The selectable filters and the shutters are interconnected through a feedback circuit to the control circuit that controls the activation of the high power laser thereby preventing lasing thereof without the correct filter or the correct protection device in place.

In a further embodiment of the present invention, the output of the harmonic generator is input through a dye laser for generation of a plurality of lasing frequencies. In this manner, any one of a multitude of frequencies are available for use in the surgical operation by tuning this dye laser.

In a yet further embodiment of the present invention, a method for delivering laser energy to the eye includes generating a laser beam and controlling the duration and power level of this laser beam. The laser beam is then optically directed to intersect the illumination axis of the slit lamp at a point radially disposed from the rotational axis such that the laser beam intersects the illumination point for all angles of the slit lamp. The output of the laser that is directed for intersection with the illumination path of the slit lamp is then optically directed along the path of the slit lamp and then focused such that it is parfocal with the illumination of the slit lamp. This permits the laser beam to be positioned by positioning the illumination of the slit lamp. It is not necessary to individually or separately position the laser. This is done in one operation by positioning the slit lamp. Other aspects of the present invention will become apparent hereinafter.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
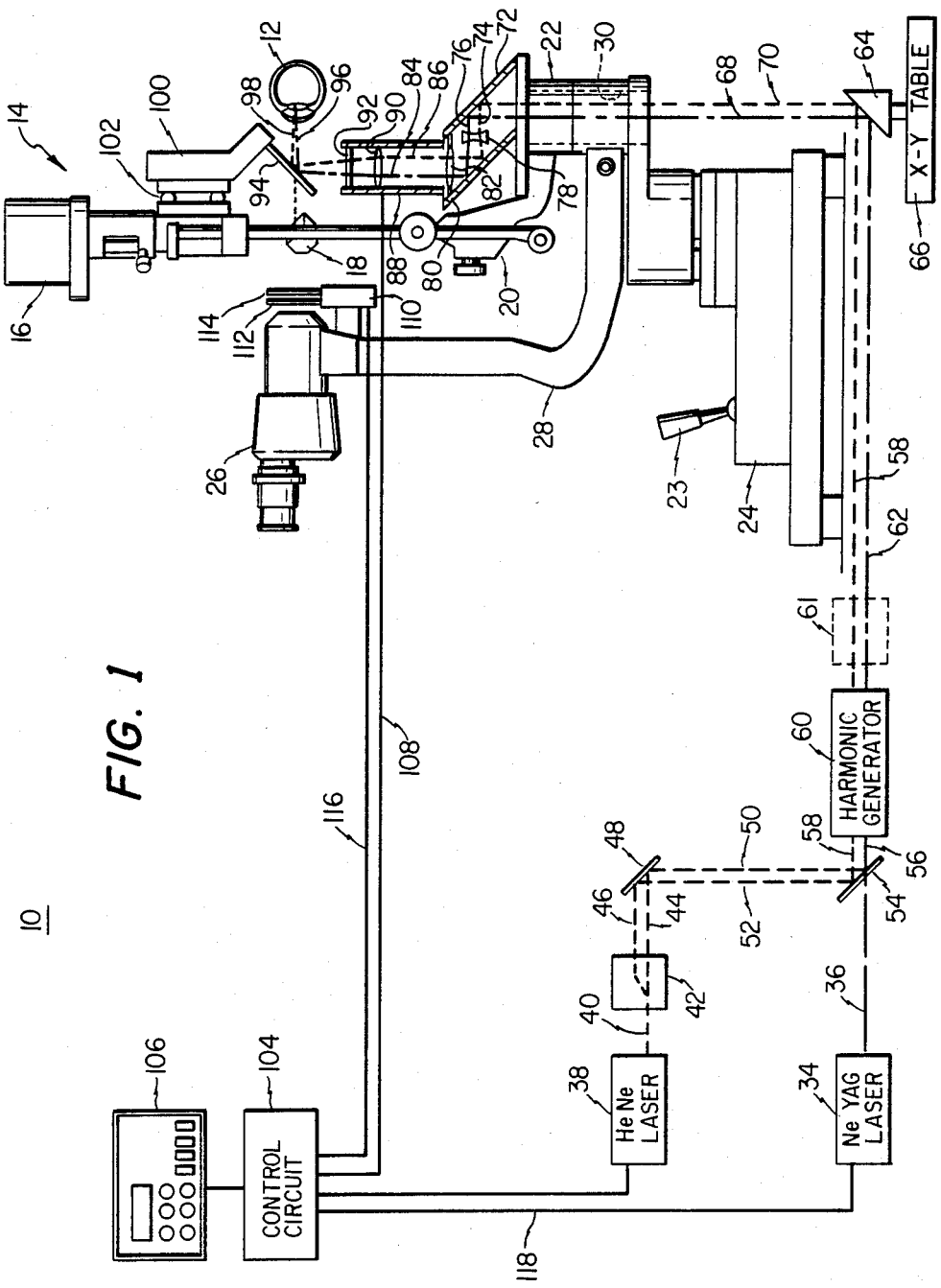
FIG. 1 illustrates a schematic diagram of the laser delivery system of the present invention.

Referring now to FIG. 1, there is illustrated a schematic view of a laser delivery system 10 for delivery of laser energy to an eye 12. A slit lamp 14 is comprised of an illuminator 16 and a mirror 18 for reflecting light originating from the illuminator 16 to the eye 12. Although not shown, the slit lamp 14 also has a lens that focuses the light from the illuminator 16 onto a specific portion of the eye that is determined by the operator. The shape of the focused light can take the form of either a slit with a defined width and heighth or a spot. The illuminator 16 and the mirror 18 are mounted on a support 20 that is "L" shaped and mounted for rotation about the lower end thereof on a rotational support 22. The rotational support 22 is rotatably mounted on a base 24 for rotation about a central axis that passes through the middle of the rotational support 22, as indicated by a center line.

The slit lamp 14 is operable to traverse an arc about the rotational axis of the rotational support 22 such that the eye, when centered on the rotational axis, allows the illumination from the slit lamp 14 to be continually focused at a selected point on the eye 12. In this manner, it is only necessary to vary the rotational position of the slit lamp 14 to illuminate a desired portion of the eye without requiring the patient to move.

A biomicroscope 26 is mounted on an "L" shaped vertical support 28 which is mounted at the lower end thereof to a rotational support 30. The rotational support 30 is mounted for rotation on the base 24 about the rotational axis of the rotational support 22. The biomicroscope 26, upon rotation, traverses a second arc about the common rotational axis of both the rotational support 22 and the rotational support 30. When the biomicroscope 26 is focused on the center line of the rotational axis, rotation about the rotational axis does not vary the position of the focal point in relation to the object being viewed. However, this focal point can be adjusted about the rotational axis such that rotation of the biomicroscope 26 results in slight movement of the focal point thereof. It should be understood that both the slit lamp 14 and the biomicroscope 26 are independently rotatable about the rotational axis to independently illuminate the eye as desired while viewing the eye at a selected angle. In most applications, the eye is normally viewed from a perpendicular position and the slit lamp 14 is rotated. The axis for viewing will hereinafter be referred to as the "viewing axis".

A high power laser 34 is operable to generate a laser beam 36 having a power in the range of 0 to 300 millijoules. The laser 34 is a Neodymium Yttrium-Aluminum Garnet laser (hereinafter referred to as "NeYAG"). The output wavelength of the laser 34 at the Fundamental frequency is 1.064 micrometers.

A low power laser 38 is operable to generate a low power laser beam 40. The laser 38 is a Helium-Neon laser (hereinafter referred to as "HeNe") which delivers a power output of approximately 2 milliwatts with the wavelength of 632.8 nanometers. This wavelength results in a frequency in the visible spectrum that emits red light. Therefore, the laser beam 40 appears as a red spot when focused on a particular point.

The laser beam 40 is input to a birefringent crystal 42 that is operable to separate nonpolarized light into two parallel laser beams 44 and 46. The parallel laser beams 44 and 46 are linearly polarized with their oscillation directions perpendicular to each other. The birefringement crystal 42 can utilize a naturally birefringement crystal such as Calcite or an electooptic birefringent crystal, such as KDP. The crystal 42 outputs the laser beams 44 and 46 in their original directions, that is, the direction of the laser beam 40, displaced by a finite distance. Thus, light made to vibrate exclusively in either direction follows a path direction in agreement of the polarization selection and appears in one of two possible positions. The light beam 44 is normally referred to as the "ordinary" ray and the light beam 46 is normally referred to as the "extraordinary" ray since it is the ray that is displaced from the original axial direction of the laser beam 40.

The laser beams 44 and 46 are directed to a mirror 48 that is oriented at a 45 degree angle with respect thereto. This reflects the laser beams 44 and 46 off at a 90 degree angle to form two redirected laser beams 50, corresponding to laser beam 44, and 52, corresponding to laser beam 46. Laser beams 50 and 52 impinge upon a dichroic mirror 54 that is oriented at a 45 degree angle thereto. The dichroic mirror 54 is operational to reflect the two laser beams 50 and 52 and it is a frequency selective reflectance, that is, the dichroic mirror 54 is transparent to other frequencies or wavelengths. The dichroic mirror 54 in the present embodiment is transparent to the wavelength of light generated by the laser 34 such that the laser beam 36 is transmitted therethrough.

The laser beam 36 is oriented such that it is colinear or coexistent with the reflected beam that results from the laser beam reflecting off the surface of the mirror 54. This results in a combined laser beam 56 that is coaxial with the laser beam 36. The laser beam 52 is reflected off the dichroic mirror to form a laser beam 58 that remains parallel to the laser beam 56 and displaced by the finite distance equal to the displacement of the laser beams 44 and 46.

The laser beams 56 and 58 are input to a harmonic generator 60 that is operable to generate harmonics of only the high power laser 34. The harmonic generator 60 is a type 2 KDAP angle tuned crystal that generates the fundamental frequency of the NeYAG laser 34 and also another frequency having a wavelength of 0.532 micrometers which is the first harmonic of the laser 34. This frequency is in the green region of the visible spectrum whereas the fundamental frequency of the laser 34 is in the infrared region. Therefore, the laser beam 56 passing through the harmonic generator 60 results in a laser beam 62 that is a combination of the ordinary ray from the crystal 42 of the low power laser 38 and a harmonic rich laser beam resulting from the high power laser beam passing through the harmonic generator 60. The laser beam 58 passes through the harmonic generator 60 without generating harmonics due to the low power thereof, thus resulting in the same laser beam 58 output therefrom.

In an alternate embodiment, a tunable dye laser 61, as shown by the phantom lines, can be utilized to generate other frequencies. To accomplish this, dye laser 61 is inserted in the output of the harmonic generator 60 and is driven therewith. The output of the harmonic generator 60 provides the excitation frequency with which the active medium in the dye laser is elevated above its oscillation threshold.

A reflecting device 64 is mounted on an X-Y table 66 at a 45 degree angle with respect to the laser beams 58 and 62. The laser beams 58 and 62 impinge upon the surface of the reflecting device 64 to be reflected along a desired path. The reflecting device 64 can either be a mirror or a pentaprism. The purpose of the pentaprism is to reflect the laser beam along an orthogonal path even though there is some fluctuation in the orientation of the laser beams 58 and 62. For example, if the angle between the reflected rays from the device 64 and the incident rays 58 and 62 is less or greater than 90, the pentaprism utilized as the reflecting device 64 will maintain the reflected rays along the desired path and orthogonal to the base of the pentaprism. The reflected beam is represented by a laser beam 68, corresponding to the laser beam 62, and a laser beam 70, corresponding to the laser beam 58. It is important to note that the X-Y table 66 is attached to the base 24 and the reflecting device 64 is aligned such that the ray 68 is colinear with the rotational axis of the rotational supports 22 and 30. It is an important aspect of the present invention that the laser beam 68, which is comprised of the ordinary ray of the laser beam 40 and the harmonic rich output of the harmonic generator 60, is aligned with the rotational axis of the rotational supports 22 and 30.

The laser beams 68 and 70 pass through the center of the rotational supports 22 and 30 to impinge upon a mirror 72 and reflect from the surface of the mirror 72 as two parallel laser beams 74, corresponding to the laser beams 70, and 76, corresponding to the laser beam 68. Laser beams 74 and 76 are passed through a negative lens 78 and are incident upon a mirror 80 disposed at a 45 degree angle thereto. The reflected laser beams from the mirror 80 are passed through an aspheric lens 82. The combination of the negative lens 78 and the aspheric lens 82 is a Gallilean optics system for expanding the beam. The output of the aspheric lens 82 is an expanded laser beam 84, corresponding to the laser beam 62, and an expanded laser beam 86, corresponding to the laser beam 58. The laser beams 84 and 86 are collimated at the output of the lens 82 for parallel transmission thereof. In expanding the laser beams, the power per square unit of area is reduced to facilitate processing by optics that may become damaged as the result of the high power per square unit of area existing in the unexpanded laser beams.

The laser beams 84 and 86 are input to a module 88 that is operable to both focus the laser beams and to provide some filtering of the laser beams. This filtering will be described hereinbelow with reference to the operation of the harmonic generator 60. The module 88 is replaceable to facilitate the use of different filters therein. The module 88 includes an aspheric lens 90 and a filter 92. Since, as described above, the laser beams 84 and 86 are parallel, the lens 90 is operational to focus the laser beams at the focal point thereof. The filter 92 is operable to select the harmonic output by the harmonic generator 60. In this manner, either infrared radiation can be selected emitted by the fundamental harmonic of the NeYAG laser 34 or the green radiation emitted by the second harmonic can be selected for the desired signal operation, as will be described hereinbelow.

The laser beams output by the module 88 impinge upon a dielectric mirror 94 that is disposed between the lens 90 and the focal point thereof. The dielectric mirror 94 is operational to reflect the frequencies contained in the laser beams 58 and 62 and processed through the optics thereafter when the laser beams are impingement upon a selected side thereof. The dielectric mirror is manufactured by Omega Optical. The laser beams impinging upon the dielectric mirror 94, which is oriented at essentially a 45 degree angle thereto, form a reflected laser beam 96, corresponding to the laser beam 62, and a reflected laser beam 98, corresponding to the laser beam 58. The laser beams 96 and 98 are shown focused on the lens of the eye 12 which is positioned approximately along the rotational axis of the rotational supports 22 and 30.

The dielectric mirror 94 is mounted on a bracket 100 that is mounted on a micromanipulator 102 for changing the position of the mirror 94 relative to the laser beams output by the module 88. The dielectric mirror 94 is positioned within the path of the light output by the slit lamp 14 and is transparent thereto due to an antireflective coating thereon. The illumination from the slit lamp 14 passing through the dielectric mirror 94 is selectively focused on the eye 12 at a desired point therein which is also the point at which the laser beams 96 and 98 are focused. The lens 90 in the module 88 is adjustable such that the position of the focal point thereof is adjustable. This allows the system 10 to initially be set up such that the focal point of the lens 90 and the focal point of the slit lamp 14 are coexistent or parfocal.

From an operational standpoint, it is to be appreciated that when the vertical support 20 is rotated about the rotational axis of the rotational support 22, the mirror 72 and the mirror 80 also rotate therewith. Since the primary laser beam 62, that is, the laser beam with the harmonic rich output of the harmonic generator 60 contained therein, is aligned along the rotational axis of the supports 22 and 30, rotation of the vertical support 20 maintains the intersection point of the laser beams 96 and 98 with the rotational axis at a fixed point. It should be understood that this is also the principal of operation of the slit lamp 14 when it is also rotated. If the focal point of the laser beams 96 and 98 is adjusted such that it is on the rotational axis of the support 20, then rotation of the vertical support 20 maintains the focal point at this exact point. However, if the focal point is not exactly aligned with the rotational axis, then the intersection point therewith is maintained. In this manner, once the laser beams 96 and 98 are focused on a point, such as the lens of the eye, the vertical support 20 can be rotated without refocusing or repositioning the laser or the optics through which the laser beams are passed. For example, if the eye 12 is positioned such that the lens therein is directly lined up with the rotational axis of the rotational support 22, the laser beams 96 and 98 can be focused onto the lens and the vertical support 20 moved without disturbing the focus.

The high power laser 34 and the low power laser 38 are controlled by a control circuit 104. The control circuit 104 is remotely operated by a control panel 106. The control circuit 104 is a simple group of relays and switches that either turn on the laser 34 or control the duration of the output therefrom. The control panel 106 merely modifies and initiates the operations therein.

A feedback circuit is formed between the control circuit 104 and the module 88 connected through a single line 108. The module 88 has a series of pins, as will be described hereinbelow, operable to "code" the module such that the control circuit 104 can differentiate between different modules. In this manner, various functions of the laser system can be linked to the type of module that is utilized for the module 88. In addition, a protection unit 110 is connected to the vertical support 28 below the viewing axis of the biomicroscope 26. The protection device 110 has a occluder 112 and an absorbing filter 114 disposed thereon which are operable to be selectively disposed within the viewing path of biomicroscope 26. The occluder 110 is operable to block the viewing path to selectively prevent radiation reflected from the surface of the eye from reflecting back to the operator or surgeon. This prevents the levels of coherent radiation that are contained in a laser beam utilized in surgical procedures from damaging the surgeon's eyes. The absorbing filter 114 is operable to effectively reject or absorb the particular frequency of the laser utilized. In this manner, protection is afforded to the surgeon's eyes. The protection device 110 is connected to the control circuit 104 by a control line 116. Microswitches (not shown) disposed in the protection device 110, are operable to prevent the control circuit 104 from activating the laser 34 until the proper filter or occluder are disposed in the viewing path.

The low power laser 38 is operable, upon splitting by the crystal 42, to provide two parallel laser beams that can be converged at the eye 12 to provide a reference for focusing the laser directing optics. Since the laser 38 is an HeNe laser, the light emitted therefrom is in the visible region, more particularly, red light. Therefore, when the lens 90 and the module 88 is not in proper focus, the two laser beams 96 and 98 do not converge at the same point that the focal point of the slit lamp 14 converges. This results in the presence of two visible spots, one for each of the laser beams 96 and 98. As noted above, the laser beam 96 includes both the ordinary ray from the crystal 42 of the low power laser 38 and the high power laser beam from the laser 34. It should be understood, however, that the laser 34 is not activated during the focusing operation.

By moving the lens 90 in a reciprocal direction along the axis of the laser beams 84 and 86, the convergent point of the laser beams 96 and 98 (focal point of the lens 90) can thereby be adjusted. This is done by observing the desired surface to lase upon and then adjusting the lens 90 until a single spot results, which is the situation that occurs when both laser beams 96 and 98 converge. Since the laser beam output by the laser 34 is coexistent with the ordinary ray of the two parallel rays output by the crystal 42, the laser beam delivered from the laser 34 is also now in focus.

To control the operation of the laser 34, the control circuit 104 is connected thereto by a signal line 118. A signal line 120 connecting the control figure to the low power laser 38 provides the power thereto. The high power laser 34 is only activated during the actual surgical procedure and then only for very small durations. It is of paramount important to control the duration and the power level of the laser. In addition, it is necessary to select the wavelength for the particular surgical operation. As will be described hereinbelow, the laser 34 is normally of a Q-switched type that allows delivery of a plurality of individual laser pulses. The duration of the total lase determines the average amount of energy delivered to the surgical area.

Figure 2:
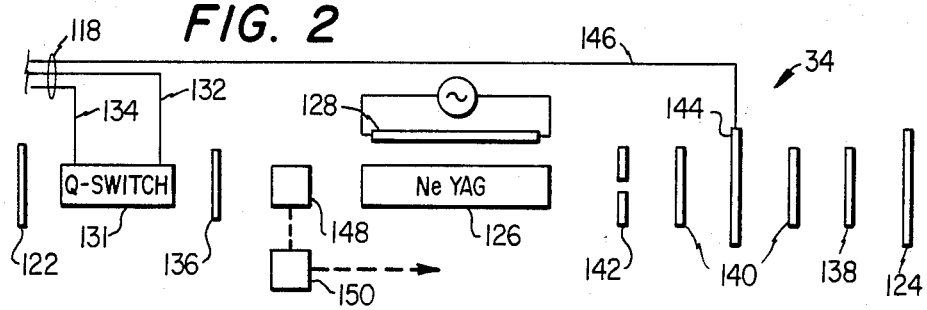
FIG. 2 illustrates a schematic diagram of the NeYAG laser for generating the high power laser beam.

Referring now to FIG. 2, there is illustrated a schematic diagram of the high power laser 34. A resonant cavity for the laser is defined by a high reflecting end mirror 122 and a high reflecting end mirror 124. A NeYAG crystal 126 is disposed between the mirrors 122 and 124 and a flash lamp 128 is disposed adjacent to the crystal 126. The crystal 126 provides the active laser medium and the flash lamp 128 is utilized to raise the electrons in the crystal 126 to a metastable state. Upon disposal in the resonant cavity formed by the mirrors 122 and 124, the resonant cavity will oscillate, thereby building up sufficient power to lase.

A Q-switch 130 is disposed in the resonant cavity and is of an electrooptic type normally referred to as a "Pockles" cell. This Q-switch can be activated by two signal lines 132 and 134 which are connected thereto for activation thereof. A half wave plate 136 is disposed between the Q-switch 131 and the crystal 126 and a half wave plate 138 is disposed between the mirror 124 and the crystal 126. A beam expander 140 is disposed between the half wave plate 138 and the crystal 136 and an aperture 142 for reducing high order transverse modes is disposed between the beam expander 140 and the crystal 126. A shutter 144 is disposed between various lenses which make up the beam expander 140 and is operable to decrease the Q of the resonant cavity. The shutter 144 is activated through a signal line 146 to open and close the shutter which effectively turns the reflectivity of one end of the resonator on and off.

To extract the energy from the resonant cavity, a polarizing cube 148 is disposed therein which deflects a portion of the laser energy at right angles to the resonant cavity. The energy from the polarizing cube 148 is input to a tuning prism 150 to change the direction thereof. The laser described above with reference to FIG. 2 is of the type "Yag 480" manufactured by Quantell which is a readily available laser. It should be understood, however, that any high powered laser providing the approximate power output of from 0 to 30 millijoules would be sufficient as long as the wavelength is aproximately 1.06 micrometers.

The Q-switch 131 disposed in the resonant cavity is operable to produce approximately ten pulses per second. This is controlled by signals input on the signal line 32 and 34 to control the Q-switch 131. In addition, the shutter 144 is also operable to shut the cavity down. For example, if it is desired to only have ten pulses in one second, then the signal input along the signal lines 132 and 134 remains constant but the laser will not lase with the shutter 144 closed, since the cavity Q is essentially reduced to zero. Although not shown, the shutter 144 can have a microswitch disposed therein such that the shutter 144 can act as an emergency shutdown mechanism, that is, the control circuit 104 of FIG. 1 is provided with a means to sense that the cavity is operational. With the use of the microswitch, the cavity can be maintained in an inhibited mode by sensing that the shutter is actually shut.

Figure 3:
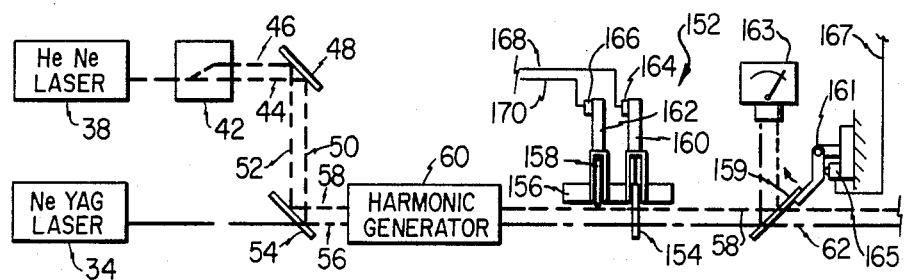
FIG. 3 illustrates an alternate embodiment of the filtering system for filtering the output of the harmonic generator.

Referring now to FIG. 3, there is illustrated an alternate embodiment of the present invention wherein the filter 92 disposed in the module 88 that selects the appropriate harmonic output by the harmonic generator 60 is replaced by a group of filters 152 that can be manually inserted into the path of the laser beam. These filters are located at the output of the harmonic generator 60 prior to being redirected by the reflecting device 64. A filter 154 is mounted for sliding upon a support 156. The filter 154 is shown disposed in the path of the laser beams 58 and 62. A filter 158 is slidably mounted on the support 156 and is shown in the retracted position such that it is not in the path of the laser beams 58 and 62. A support member 160 is attached to the filter 154 for sliding the filter through the support 156 and a support member 162 is attached to the filter 168 for sliding movement thereof. The filters 154 and 158 are manually operated to select one of the harmonics. In an exemplary embodiment, the filter 154 passes the harmonic having a wavelength of approximately 0.532 micrometers which is the green radiation and the filter 158 passes the wavelength of 1.062 micrometers and rejects the remaining portion of the spectrum. In this manner, either the fundamental or the first harmonic of the laser 34 output by the harmonic generator 60 can be selected.

A microswitch 164 is disposed on the support 156 and is operable to sense the position of the filter 158. A microswitch 166 is disposed on the support 156 to sense the position of the filter 162. The microswitches 164 and 166 are connected to the control circuit 104 of FIG. 1 through signal lines 168 and 170, respectively. In this manner, the control circuit 104 can sense the position of the filters thereby prohibiting the generation of undersired power levels for a given operation. For example, in operations requiring the use of green radiation, the filter 154 is disposed in the path of the laser beams 58 and 62 to select green radiation. This radiation of utilized for operations such as photocoagulation of red tissue. In other operations requiring the use of infrared radiation, the filter 158 is disposed in the path of the light beams 58 and 62 for such operations as capsulotomies.

The embodiment of FIG. 3 allows the insertion of the selecting filters for the harmonics output by the harmonic generator 60 to be independent from the focusing lens 90 that focuses the laser beam to be parfocal with the slit lamp. In this manner, it is not necessary to replace both the filter and the focusing lens each time a different operation is performed.

A mirror 159 is mounted on a rotating bracket 161 for rotation thereon. The mirror 159 is operable to be rotated into the path of the laser beams 58 and 62 to reflect them at a right angle thereto for sensing with a power meter 163. The reflected laser beams 58 and 62 are shown as phantom lines. It should be understood that when the mirror 159 is rotated in line with the laser beams 58 and 62, delivery of laser energy to the eye is inhibited. Rotation of the mirror 159 away from the path of the laser beams 58 and 62 allows delivery of laser energy to the eye.

A microswitch 165 is disposed on the bracket 161 to sense the position of the mirror 159. The microswitch 165 is connected to the control circuit 104 through a signal line 167 such that the microswitch 165 is in a feedback circuit. In operation, the mirror 159 is rotated into the path of the laser beams 58 and 62 prior to any surgical operations. This enables direct measurement of the actual power output by the harmonic generator 60 and the filters 154 and/or 158. The control circuit 104 prevents activation of the high power laser 34 in any mode without first checking the power level of the laser energy utilized for the particular surgical procedure. Although not shown, the power meter 163 can be connected to the control circuit 104 and the required power levels stored in memory for comparison. This would allow fully automatic operation to further protect the patient from the possibility of inadvertently applying too much power.

Figure 4:
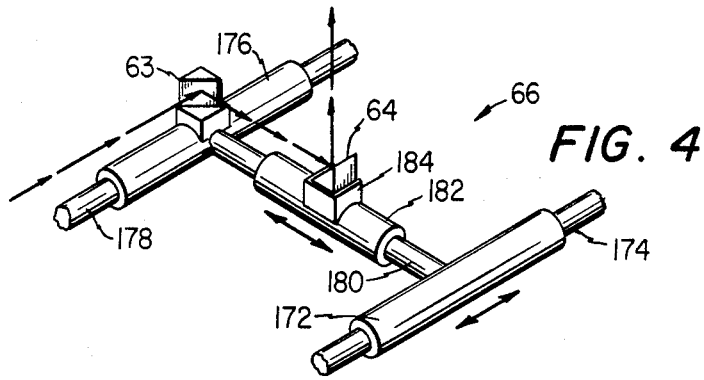
FIG. 4 illustrates a perspective view of the X-Y positioning system.

Referring now to FIG. 4, there is illustrated a perspective view of the X-Y table 66 of FIG. 1. A linear bearing 172 is concentrically disposed about a rod 174 for lateral movement along the longitudinal axis thereof. A linear bearing 176 is concentrically disposed about a rod 178 for movement along the longitudinal axis thereof. The longitudinal axis of the rods 174 and 178 are parallel to each other and a rod 180 is mounted perpendicular to each of the bearings 172 and 176 and mounted therebetween. A linear bearing 182 is concentrically mounted around the rod 182 for movement along the longitudinal axis thereof. A support bracket 184 is mounted on top of the linear bearing 182 parallel to the plane formed by the rods 174, 178 and 180. A reflecting device 63 is mounted on the linear hearing 176 to reflect a laser beam directed along the longitudinal axis of the rod 178 to a direction orthogonal thereto along the longitudinal axis of the rod 180. The redirected beam is then incident on the reflecting device 64 which is mounted on the bracket 184 such that a laser beam directed in the plane of the rods 174, 178 is deflected at right angles thereto.

The linear bearings 172 and 176 are operable to move in a first direction and the linear bearing 182 is operable to move in an orthogonal direction thereto. Linear bearings 172 and 176, since they are connected together by the rod 180, move in unison providing a first degree of freedom. The linear bearing 182 moves in an orthogonal direction providing a second degree of freedom such that adjustment of the bearings results in movement about a coordinate axis. The linear bearings 172, 176 and 182 provide a very stable adjustable positioning device for movement in one plane.

Figure 5A:
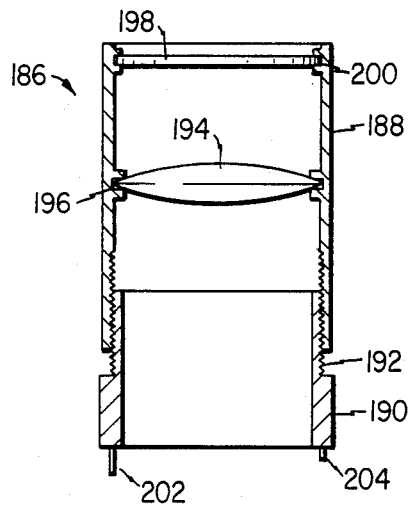
FIGS. 5a-5b illustrate cross-sectional views of various embodiments of the replaceable filters and focusing lenses.
Figure 5B:
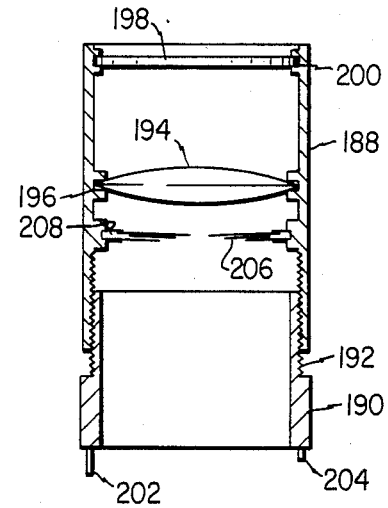

Referring now to FIGS. 5a-5b, there is illustrated cross-sectional views of two variations of the module 88 of FIG. 1. Referring specifically to FIG. 5a, there is illustrated a module 186 that is comprised of an upper tubular housing 188 and a lower tubular housing 190 threadedly connected together by threads 192. A lens 194 is disposed in a slot 196 disposed around the inner-circumference of the upper housing 188. A filter 198 is disposed in a slot 200 disposed around the inner periphery of the upper housing 188 and disposed at the end of the tubular housing 188. Coded pins 202 and 204 ar disposed around the lower edge of the housing 190 for insertion into sockets (not shown) that allow the control circuit 104 to identify the particular module 88 that is being inserted into the sockets (not shown).

The filter 198 in the present embodiment can be either red or green. The red filter is operable to absorb green radiation that is generated at the wavelength of 0.532 micrometers output by the harmonic generator 60 and transmit infrared radiation. The lens 194 is the focusing lens corresponding to the lens 90 of FIG. 1, with a focal length of approximately 50 millimeters. The upper housing 188 is rotatable on the threads 192 such that it reciprocates along the central axis of the lens 194 thereby positioning the focal point of the lens 194.

The green filter utilized as filter 198 selects the green radiation that is contained in a first harmonic of the laser beam output by the harmonic generator 60 and is transmissive thereto. The coded pins 202 and 204 are different for this filter such that the control circuit 104 recognizes that a different filter is in the system. The purpose for this is that various levels of power must be output by the laser 38 depending upon first, the operation to be performed and second, the type of filter inserted therein. For example, operations such as a capsulotomy require a power level of between 0 and 30 millijoules. This power level is contained in the fundamental harmonic in the infrared region. When the laser is utilized in operations to coagulate tissue, the harmonic emitting in the green region is utilized since blood vessels that contain hemoglobin which is red tend to absorb highly in the green region. Since the green radiation is contained in a first harmonic output by the harmonic generator 60, it is necessary to filter out the fundamental harmonic. The reason for this is that the fundamental harmonic normally contains not only the different wavelength which results in different absorbtive properties in the tissue but also has a different power level. The first harmonic tends to have a lower power level which requires the power initially output by the laser 34 to be increased. Since this also increases the power in the fundamental harmonic, it is important that the power setting be synchronized with the type of filter such that it is not possible for the higher power level required for operation with the first harmonic to exist when operating with the fundamental harmonic of the laser 34. This is done by sensing the pins 202 and 204 to determine what type of filter is disposed therein.

The lens 194 is an achromatic difraction limited lens that produces a selected spot size. The spot size normally is approximately 43 microns which can be varied depending upon the size of the area to be operated upon and the amount of power per unit square area that is to be delivered to the operating area. In applications that require the laser energy to be focused over a large area, a lens having a very poor focal point is utilized for the lens 194. This allows the lens to be focused on a spot and energy from the laser dissipated over a large area. An operation of this type would involve such things as vaporizing a cataract. In this operation, the laser energy must be directed at the desired area for a larger amount of time than the short durations required for photocoagulation of blood vessels.

Referring now to FIG. 5b, there is illustrated an alternate embodiment of the device illustrated in FIG. 5a wherein like numerals refer to like parts in the two figures. A variable aperture 206 is disposed between the lens 194 and the coded pins 202 and 204 in a slot 208 disposed about the periphery of the housing 188. The variable apperture 206 is operable to diffract the laser beam to spread out the beam thereby resulting in a larger spot. By varying the aperature, the spot size can be adjusted which directly varys the power per unit square area.

Figure 6:
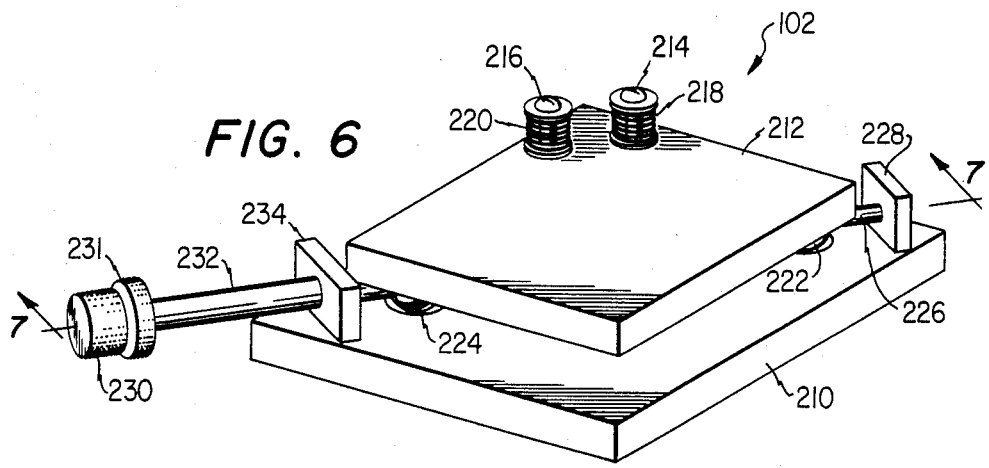
FIG. 6 illustrates a perspective view of the micromanipulator.

Referring now to FIG. 6, there is illustrated a prospective view of the micromanipulator 102 of FIG. 1. The micromanipulator 102 includes a mounting base 210 and a floating mounting surface 212. The mounting surface 212 is disposed above the mounting base 210 a defined distance and is attached to the mounting base 210 by two standoff screws 214 and 216. The screws 214 and 216 have springs 218 and 220, respectively, disposed between the heads thereof and the top surface of the mounting surface 212. A spring (not shown) is disposed between the bottom surface of the mounting surface 212 and the top surface of the mounting base 210. The remaining portion of the mounting surface 212 is supported by a floating ball 222 and a floating ball 224. A rod 226 is disposed through the ball 222 and attached thereto and rotatable within a bearing 228 and passing underneath the mounting surface 212 to connect to a knob 234 for rotation thereof. The ball 224 is connected to a tubular member 232 that rotates in a bearing 234 with a knob 231. The attachment points to the balls 222 and 224 are diposed off center with the center axis of the balls such that rotation of the ball causes a reciprocating motion of the mounting surface 212. In this manner, there are defined three points on the under surface of the mounting surface 212. One point is in the vicinity of the two screws 214 and 216, the second point is at the contact surface of the ball 222 and the third point is at the contact point of the ball 224. Therefore, essentially three points are defined and movement of two of these points (the contact points of the balls 222 and 224) allow three dimensional movement of the mounting surface 212.

Figure 7:
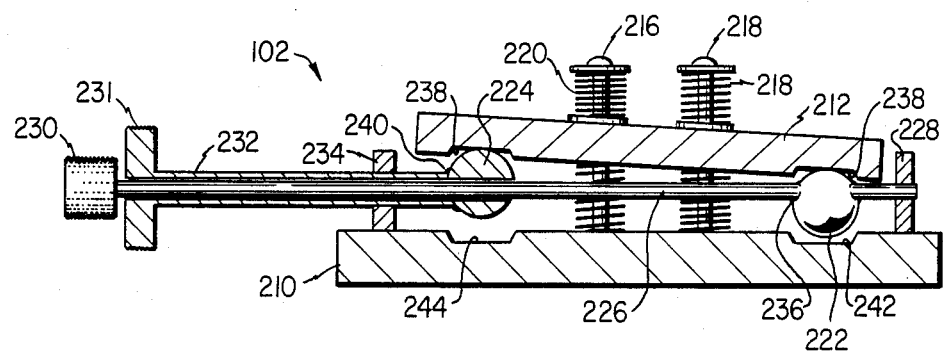
FIG. 7 illustrates a side view of the micromanipulator taken along line 7—7 of FIG. 6.

Referring now to FIG. 7, there is shown a cross-sectional diagram of the micromanipulator 102 taken along line 7—7 of FIG. 6 wherein like numerals refer to like parts in the figures. The rod 226 passes through both the ball 224 and the ball 222 for rotation within the tube 232 and the bearing 228. The rod 226 is attached to the ball 224 at a point 236. It should be noted that the hole disposed through the ball 222 and the hole disposed in ball 226 are not along the center lines, that is, they are off center. In this manner, rotation of the ball 224 about the axis of the rod 226 causes a reciprocating motion of the mounting surface 212.

The tube 232 is attached to the ball 234 at a point 238 that goes around the circumference thereof. This allows the ball 224 to rotate with the tube 232. The tube 232 is attached to the ball 224 with its longitudinal axis off center with respect to the central axis of the ball 224. In this manner, rotation of the ball 224 translates a reciprocal motion to the mounting surface 212 in a similar manner to that of the ball 222. The mounting surface 212 has a recess 238 and a recess 240 for receiving the balls 222 and 224, respectively, and the mounting base 212 has a recess 242 and 244 for receiving the balls 222 and 244, respectively. The recesses permit the dimensions of the mounting surface 212 and the mounting base 210 to be reduced for a given size ball.

The micromanipulator 102 allows a three-dimensional movement of the dielectric mirror 94 such that the focused laser beam can be positioned within the illumination area of the slit lamp. For example, if an area of the eye is illuminated with a slit of light having a defined width and heighth, the focused laser spot, which is typically around 14 microns, can be manipulated within the illuminated area and, in some instances, to areas outside of the illuminated area for positioning therein. This is essentially a "fine tuning" of the laser beam position. In this manner, the micromanipulator 102 provides the ability to finely position the laser beam while retaining the stability of the optical system which is of paramount importance in any laser surgery device.

In summary, a system has been described that allows laser energy to be delivered from a laser that is fixed to a stable base and separate from the slit lamp and optically directed for rotation with the slit lamp. The laser beam is directed along the rotational axis of the slit lamp and then optically directed such that it is radially removed from the rotational axis of the slit lamp to a point intersecting the illumination path of the slit lamp. The illumination of the slit lamp and the laser beam are then mixed with the laser beam diverted along the illumination path and focused parafocal with the slit lamp illumination. In this manner, rotation of a slit lamp also rotates the directional optics thereby rotating the laser beam and maintaining the laser beam focused with the slit lamp illumination. In this manner, any adjustment of the slit lamp results in an automatic adjustment of the laser beam position. In addition, this laser beam is now delivered off axis from the perpendicular with respect to the eye which normally is the viewing axis. This prevents laser energy from impinging perpendicular to the eye such that no radiation enters the eye and impinges upon sensitive points such as the macula.

Although the preferred embodiment has been described in detail, it should be understood that various changes, substitutions, and alterations can be made therein without departing from the spirit and scope of the invention as defined by the appended claims.

What is claimed is:

1. An apparatus for delivering high power laser energy to the eye for surgical operations thereon comprising:
   a hollow cylindrical member mounted on and perpendicular to a base, the interior of said cylindrical member communicating with the underside of said base;
   a biomicroscope for viewing the eye and mounted for movement about a rotational axis to traverse a first arc, said rotational axis corresponding to the longitudinal axis of said cylindrical member;
   a slit lamp mounted for movement about said rotational axis to traverse a second arc;
   a Neodymium Yttrium-Aluminum Garnet laser for generating a high energy laser beam directed parallel to the plane of said base;
   a control circuit for controlling the duration of said high energy laser beam;
   a Helium Neon laser for generating a low power laser beam;
   a birefringent crystal disposed in the path of said low energy laser beam for generating the ordinary and extraordinary rays thereof, said rays being parallel and having a defined distance therebetween;
   means for mixing the output of said high energy laser and said birefringent crystal such that said high energy laser beam is coexistent with one of the beams output by said birefringent crystal;
   a harmonic generator disposed in the path of the combined high and low energy laser beams for generating harmonics of said high energy laser beam;
   a pentaprism mounted below said base and proximate the longitudinal axis of said cylindrical member and disposed in the path of the laser beams output by said harmonic generator for providing an orthogonal deflection thereof upward into the interior of said cylindrical member;
   means for adjusting the position of said pentaprism to direct said deflected beams along said rotational axis;
   means for optically directing the output of said pentaprism along said rotational axis to intersect the illumination path of said slit lamp at a point radially disposed from said rotational axis such that said intersection point is maintained constant for all rotational angles of said slit lamp;
   a Galliliean beam expander disposed in the path of said high and low energy laser beams prior to said intersection point;
   a focusing lens disposed in the path of said high and low energy beams between said intersection point and said beam expander;
   a replaceable filter disposed in the path of said high and low energy beams between said focusing lens and said intersection point for selecting one of the harmonics of said high energy laser beam;
   coding means associated with said replaceable filter for coding each filter such that said control circuit controls the duration and power level of said high energy laser beam automatically with the selection of said filter;
   a dielectric mirror disposed at said intersection point to reflect the output of said selected filter and transmit the illumination of said slit lamp to the eye such that said high and low energy beams transmitted through said filter are parfocal with the output of said slit lamp and the illumination of said slit lamp passing through said dielectric mirror;
   means for adjusting the position of said dielectric mirror to adjust the focal point of said high energy laser beam within the illuminated area of the eye illuminated by said slit lamp; and
   a shutter disposed along the viewing axis of said slit lamp and out of the path of said high energy laser beam;
   means for activating said shutter in response to the generation of said high energy laser beam to prevent reflection of the energy from said high energy laser beam from passing along the viewing axis of said slit lamp to the operator; and
   filter means disposed along the viewing axis of said slit lamp and out of the transmission path of said high energy laser beam, said filter means selectable to filter out reflections of said high energy laser beam to the operator.

2. The apparatus of claim 1 for preventing delivery of excessive power levels to the the eye during laser surgery, further comprising:
   means for controlling the duration and output power of said laser;
   means for measuring the power level of said laser;
   means for selectively diverting the laser beam output by said laser from the eye to said power measuring means to measure power level thereof; and
   means connected to said controlling means for inhibiting activation of said laser unless the power level is measured prior to activation thereof.

* * * * *

UNITED STATES PATENT AND TRADEMARK OFFICE
CERTIFICATE OF CORRECTION

PATENT NO. : 4,520,816
DATED : June 4, 1985
INVENTOR(S) : Ronald A. Schachar, et al.

It is certified that error appears in the above-identified patent and that said Letters Patent is hereby corrected as shown below:

Col. 3, line 48   "heighth" should be --height--.

Col. 4, line 19   delete "a power" and insert --an energy output--.

Col. 6, line 68   "principal" should be --principle--.

Col. 7, line 59   "is not" should be --are not--.

Col. 8, line 18   "paramount important" should be --paramount importance--;

Col. 8, line 38   "Q-switch 130" should be --Q-switch 131--;

Col. 8, line 46   "crystal 136" should be --crystal 126--.

Col. 8, line 66   "aproximately" should be --approximately--.

Col. 9, lines 1 and 2   "line 32 and 34" should be --lines 132 and 134--.

Col. 9, line 53   "radiation of" should be --radiation is--.

Col. 10, line 41   "linear hearing" should be --linear bearing--.

UNITED STATES PATENT AND TRADEMARK OFFICE
CERTIFICATE OF CORRECTION

PATENT NO. : 4,520,816
DATED : June 4, 1985
INVENTOR(S) : Ronald A. Schachar, et al.

It is certified that error appears in the above-identified patent and that said Letters Patent is hereby corrected as shown below:

Col. 11, line 2                  "ar" should be --are--;

Col. 11, line 11               "transmit" should be --transmits--.

Col. 11, line 27               delete "a power" and insert --an energy--;

Col. 12, line 3                 "apperture 206" should be --aperture 206--;

Col. 12, line 5                 "aperature" should be --aperture--;

Col. 12, lines 8 & 9           "prospective" should be --perspective--;

Col. 12, line 28               "diposed" should be --disposed--;

Col. 12, line 46               "224 at a point 236." should be --222 at a point 236.--;

Col. 12, line 48               "ball 226 are not" should be --ball 224 are not--;

Col. 12, line 49               "ball 224 about" should be --ball 222 about--;

Col. 12, line 52               "ball 234 at a point 238" should be --ball 224 at a point 240--;

UNITED STATES PATENT AND TRADEMARK OFFICE
CERTIFICATE OF CORRECTION

PATENT NO. : 4,520,816
DATED : June 4, 1985
INVENTOR(S) : Ronald A. Schachar, et al.

It is certified that error appears in the above-identified patent and that said Letters Patent is hereby corrected as shown below:

Col. 12, line 60      "240 for receiving"
        should be --239 for receiving--;

Col. 12, line 62      "212 has a recess"
        should be --210 has a recess--.

Col. 13, line 3       "heighth" should be
        --height--.

Col. 14, line 18 (Claim 35, line 53), "Galliliean beam"
        should be --Gallilean beam--;

Col. 14, line 57 (Claim 36, line 2), delete "the", second
        occurrence.

Signed and Sealed this

Seventh Day of January 1986

[SEAL]

*Attest:*

DONALD J. QUIGG

*Attesting Officer*  *Commissioner of Patents and Trademarks*